US009056059B2

(12) United States Patent
First

(10) Patent No.: US 9,056,059 B2
(45) Date of Patent: *Jun. 16, 2015

(54) COSMETIC NEUROTOXIN COMPOSITIONS AND METHODS

(71) Applicant: Allergan, Inc., Irvine, CA (US)

(72) Inventor: Eric R. First, Morristown, NJ (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/143,316

(22) Filed: Dec. 30, 2013

(65) Prior Publication Data

US 2014/0112967 A1    Apr. 24, 2014

Related U.S. Application Data

(63) Continuation of application No. 12/695,105, filed on Jan. 27, 2010, now Pat. No. 8,647,639, which is a continuation of application No. 10/957,004, filed on Oct. 1, 2004, now abandoned.

(51) Int. Cl.
| *A61K 38/48* | (2006.01) |
| *A61K 8/66* | (2006.01) |
| *A61K 8/64* | (2006.01) |
| *A61Q 19/08* | (2006.01) |
| *A61K 8/02* | (2006.01) |

(52) U.S. Cl.
CPC ... *A61K 8/66* (2013.01); *A61K 8/64* (2013.01); *A61Q 19/08* (2013.01); *A61K 38/4893* (2013.01); *C12Y 304/24069* (2013.01); *A61K 8/025* (2013.01); *A61K 8/0241* (2013.01); *A61K 2800/654* (2013.01)

(58) Field of Classification Search
CPC ......... A61K 38/48; A61K 9/001; A61K 8/64; A61K 2039/55544
USPC ...................................... 424/239.1
See application file for complete search history.

(56) References Cited

U.S. PATENT DOCUMENTS

| 5,019,400 A | 5/1991 | Gombotz et al. ............ 424/497 |
| 5,407,609 A | 4/1995 | Tice et al. ...................... 264/4.6 |
| 5,415,864 A | 5/1995 | Kopecek et al. ............. 424/436 |
| 5,437,291 A | 8/1995 | Pasricha ........................ 128/898 |
| 5,635,215 A | 6/1997 | Boschetti ..................... 424/501 |
| 5,648,100 A | 7/1997 | Boschetti et al. ............ 424/501 |
| 5,670,484 A | 9/1997 | Binder ............................ 514/14 |
| 5,714,468 A | 2/1998 | Binder ............................ 514/14 |
| 5,766,605 A | 6/1998 | Sanders .................... 424/239.1 |
| 5,854,382 A | 12/1998 | Loomis ......................... 528/354 |
| 5,877,224 A | 3/1999 | Brocchini et al. .......... 514/772.2 |
| 5,980,948 A | 11/1999 | Goedemoed et al. ......... 424/489 |
| 5,989,545 A | 11/1999 | Foster ........................ 424/183.1 |
| 6,005,020 A | 12/1999 | Loomis ......................... 523/105 |
| 6,063,768 A | 5/2000 | First .............................. 514/14 |
| 6,139,845 A | 10/2000 | Donovan .................... 424/236.1 |
| 6,165,500 A * | 12/2000 | Cevc ............................ 424/450 |
| 6,194,006 B1 | 2/2001 | Lyons et al. .................. 424/489 |
| 6,218,440 B1 | 4/2001 | Kitagawa ....................... 521/56 |
| 6,265,379 B1 | 7/2001 | Donovan ......................... 514/14 |
| 6,299,893 B1 | 10/2001 | Schwartz ..................... 424/422 |
| 6,306,403 B1 * | 10/2001 | Donovan .................... 424/239.1 |
| 6,306,423 B1 | 10/2001 | Donovan et al. ............. 424/423 |
| 6,312,708 B1 * | 11/2001 | Donovan ...................... 424/423 |
| 6,316,522 B1 | 11/2001 | Loomis et al. ................ 523/105 |
| 6,358,926 B2 | 3/2002 | Donovan ........................ 514/14 |
| 6,379,703 B1 | 4/2002 | Lyons et al. .................. 424/489 |
| 6,383,509 B1 | 5/2002 | Donovan ...................... 424/423 |
| 6,423,319 B1 | 7/2002 | Brooks ....................... 424/239.1 |
| 6,436,424 B1 * | 8/2002 | Vogel et al. .................. 424/422 |
| 6,451,240 B1 | 9/2002 | Sherman et al. ............. 264/504 |
| 6,458,365 B1 | 10/2002 | Aoki ................................ 514/2 |
| 6,464,986 B1 | 10/2002 | Aoki ................................ 514/2 |
| 6,506,399 B2 * | 1/2003 | Donovan ...................... 424/423 |
| 6,579,847 B1 * | 6/2003 | Unger .......................... 514/19.2 |
| 6,585,993 B2 * | 7/2003 | Donovan et al. ............. 424/423 |
| 6,596,316 B2 | 7/2003 | Lyons et al. .................. 424/489 |
| 6,620,415 B2 | 9/2003 | Donovan .................... 424/239.1 |
| 6,660,301 B1 | 12/2003 | Vogel et al. .................. 424/489 |
| 6,790,456 B2 | 9/2004 | Vogel et al. .................. 424/423 |
| 6,827,931 B1 | 12/2004 | Donovan .................... 424/239.1 |
| 6,939,033 B2 | 9/2005 | Lyons et al. .................. 366/348 |
| 6,977,080 B1 * | 12/2005 | Donovan ................... 424/247.1 |

(Continued)

FOREIGN PATENT DOCUMENTS

| FR | 2378808 | 8/1978 | |
| WO | WO 01/93890 | 12/2001 | ............ A61K 38/00 |
| WO | WO 2004/062651 | 7/2004 | ............... A61K 9/72 |

OTHER PUBLICATIONS

Sharp, JS et al, Macromolecules, 2001, vol. 34, pp. 8752-8760, Swelling of Poly(DL-lactide) and Polylactide-co-glycolide in Humid environments.*

(Continued)

*Primary Examiner* — Albert Navarro
*Assistant Examiner* — Ginny Portner
(74) *Attorney, Agent, or Firm* — Brigitte C. Phan; Ted A. Chan; Debra D. Condino

(57) ABSTRACT

Cosmetic compositions include a Clostridial neurotoxin component and a microsphere component. In certain compositions, the composition includes a botulinum toxin and a plurality of swellable microspheres. The compositions are administered to individuals, by injection and the like, to treat a cosmetic defect of deficiency.

18 Claims, No Drawings

(56) References Cited

U.S. PATENT DOCUMENTS

| | | | | |
|---|---|---|---|---|
| 7,015,192 | B1 | 3/2006 | Mira et al. | 514/200 |
| 7,074,426 | B2 | 7/2006 | Kochinke | 424/435 |
| 7,179,474 | B2 | 2/2007 | First | 424/239.1 |
| 7,291,497 | B2 | 11/2007 | Holmes et al. | 435/287.2 |
| 7,357,934 | B2* | 4/2008 | Donovan et al. | 424/239.1 |
| 7,429,386 | B2 | 9/2008 | First | 424/236.1 |
| 7,473,679 | B2 | 1/2009 | Blanes Mira et al. | 514/200 |
| 7,485,624 | B2 | 2/2009 | Donovan | 514/12 |
| 7,591,806 | B2 | 9/2009 | Xu | 604/173 |
| 7,691,381 | B2 | 4/2010 | Hughes | 424/184.1 |
| 7,780,967 | B2* | 8/2010 | Hunt | 424/236.1 |
| 7,838,007 | B2* | 11/2010 | Brin et al. | 424/236.1 |
| 8,647,639 | B2* | 2/2014 | First | 424/234.1 |
| 8,658,391 | B2* | 2/2014 | Edelson | 435/20 |
| 2002/0028216 | A1 | 3/2002 | Donovan | 424/236.1 |
| 2002/0081304 | A1* | 6/2002 | Elmore et al. | 424/180.1 |
| 2002/0086036 | A1 | 7/2002 | Walker | 424/236.1 |
| 2002/0094339 | A1* | 7/2002 | Brin et al. | 424/247.1 |
| 2002/0098237 | A1 | 7/2002 | Donovan et al. | 424/484 |
| 2003/0202990 | A1 | 10/2003 | Donovan et al. | 424/239.1 |
| 2003/0211121 | A1 | 11/2003 | Donovan | 424/247.1 |
| 2003/0224020 | A1 | 12/2003 | Zabudkin et al. | 424/239.1 |
| 2004/0009180 | A1 | 1/2004 | Donovan | 424/449 |
| 2004/0033241 | A1* | 2/2004 | Donovan | 424/239.1 |
| 2004/0058313 | A1 | 3/2004 | Abreu | 435/5 |
| 2004/0086531 | A1 | 5/2004 | Barron | 424/239.1 |
| 2004/0086532 | A1 | 5/2004 | Donovan | 424/239.1 |
| 2004/0143213 | A1 | 7/2004 | Hunter et al. | 604/93.1 |
| 2004/0151741 | A1 | 8/2004 | Borodic | 424/239.1 |
| 2004/0170665 | A1* | 9/2004 | Donovan | 424/427 |
| 2004/0192658 | A1 | 9/2004 | Hunter et al. | 514/152 |
| 2004/0220100 | A1 | 11/2004 | Waugh et al. | 514/12 |
| 2004/0253274 | A1* | 12/2004 | Voet | 424/239.1 |
| 2005/0053655 | A1 | 3/2005 | Yang et al. | 424/464 |
| 2005/0214327 | A1 | 9/2005 | Brooks et al. | 424/239.1 |
| 2005/0214328 | A1 | 9/2005 | Zeldis et al. | 424/239.1 |
| 2005/0220821 | A1 | 10/2005 | First | 424/239.1 |
| 2006/0057165 | A1 | 3/2006 | Dimitrakoudis et al. | 424/239.1 |
| 2006/0058513 | A1* | 3/2006 | Papisov et al. | 530/409 |
| 2006/0153876 | A1* | 7/2006 | Sanders | 424/239.1 |
| 2006/0173709 | A1 | 8/2006 | Traynor et al. | 705/2 |
| 2006/0252674 | A1 | 11/2006 | Peritt et al. | 514/11 |
| 2007/0020295 | A1 | 1/2007 | Donovan | 424/239.1 |
| 2007/0270732 | A1* | 11/2007 | Levin et al. | 604/20 |
| 2008/0226690 | A1 | 9/2008 | DeAngelis | 424/423 |
| 2009/0036403 | A1 | 2/2009 | Stroumpoulis et al. | 514/54 |

OTHER PUBLICATIONS

Aoki K., et ai, "Mechanisms of the antinociceptive effect of subcutaneous Botox: Inhibition of peripheral and central nociceptive processing," Cephalalgia Sep. 2003;23(7):649.
Bigalke H., et al., "Botulinum A Neurotoxin Inhibits Non-Cholinergic Synaptic Transmission in Mouse Spinal Cord Neurons in Culture," Brain Research 360;318-324:1985.
Bigalke H., et al., "Tetanus Toxin and Botulinum A Toxin Inhibit Release and Uptake of Various Transmitters, as Studied with Particulate Preparations From Rat Brain and Spinal Cord," Naunyn-Schmiedeberg's Arch Pharmacol 316;244-251: 1981.
Binz T. et al., "The Complete Sequence of Botulinum Neurotoxin Type A and Comparison with Other Clostridial Neurotoxins." J Biochem (Tokyo) Jun. 5, 1990; vol. 265(16);9153-9158.
Boschetti et al. (Bull. Soc. Chim., No. 4 France (1986)).
E. Boschetti. Microspheres for Biochromatography and Biomedical Applications. Part I, Preparation of Microbeads in Microspheres. Microencapsulation and Liposomes, John Wiley & Sons. Arshady R., Ed., 2:171-189 (1999).
Bushara K., "Botulinum toxin and rhinorrhea," Otolaryngol Head Neck Surg 1996; 114(3):507.

Coffield et al., "The Site and Mechanism of Action of Botulinum Neurotoxin," Jankovic J. ed.,Neurological disease and therapy. Therapy with botulinum toxin, Marcel Dekker, Inc., (1994), p. 5.
de Maio, Mauricio, Cosmetic and Laser Therapy, 2003, vol. 5, pp. 210-212, Dec. 2003.
Gonell•Gispert et al., "Snap-25a and -25b isoforms are both expressed in insulin-secreting cells and can function in insulin secretion," Biochem J 1 ;339 (pt 1): 159-165: 1999.
Habermann, "I-Labeled Neurotoxin from ClostridiumBotulinum A: Preparation, Binding to Synaptosomes and Ascent to the Spinal Cord," Nauny-Schmiedeberg's Arch. Pharmacol. (1974) 281:47-56.
Habermann E., "Inhibition by Tetanus and Botulinum A Toxin of the release of [3H] Noradrenaline and [3H]GABA From Rat Brain Homogenate," Experientia 44;224-226:1988.
Habermann E., et al., "Tetanus Toxin and Botulinum A and C Neurotoxins Inhibit Noradrenaline Release From Cultured Mouse Brain," J Neurochem 51(2);522-527:1988) CGRP.
Jacks, I., et al., "Idiopathic toe walking: Treatment with botulinum toxin A injection," Dev Med Child Neurol (2002) 44 (Suppl 91 ):6.
Katsambas A, et al., "Cutaneous diseases of the foot: Unapproved treatments," Clin Dermatol; Nov.-Dec. 2002;20(6):689-699.
Langhein, C et ai, Journal of Applied Bacteriology, vol. 63,1987, pp. 443-448, Antibody response to bacterial antigens covalently bound to biodegradable polymerized serum albumin beads.
Langer, Robert, Methods of Drug Delivery, Science, Sep. 28, 1990, vol. 249 (4976), pp. 1527-1533.
Li Y., et al., "Sensory and motor denervation influence epidermal thickness in rat foot glabrous skin," Exp Neurol (1997) 147:452-462 (see p. 459).
Mov Disord, 10(3):376:1995.
Moyer E et al., "Botulinum Toxin Type B: Experimental and Clinical Experience," being chapter 6, pp. 71-85 of "Therapy With Botulinum Toxin", edited by Jankovic, J. et al. (1994), Marcel Dekker, Inc.
Naoum, Christos et ai, International Journal of Dermatology, 2001, vol. 40, pp. 609-621, Dermal filler materials and botulin toxin.
Naumann et al., "Botulinum toxin type A in the treatment of focal axillary and palmar hyperhidrosis and other hyperhidrotic conditions," European J. Neurology 6 (Supp 4): S111-S1150 (1999).
Pearce, L.B., "Pharmacologic Characterization of Botulinum Toxin for Basic Science and Medicine," Toxicon 35(9); 1373-1412 at 1393 (1997).
Ragona et al., "Management of Parotid Sialocele with Botulinum Toxin," The Laryngoscope 109:1344-1346:1999.
Rogers J., et al., "Injections of botulinum toxin A in foot dystonia," Neurology Apr. 1993;43(4 Suppl 2):A329.
Sanchez-Prieto, J., et al., "Botulinum Toxin A Blocks Glutamate Exocytosis From Guinea Pig Cerebral Cortical Synaptosomes," Eur J. Biochem 165;675-681 :1897.
Sevim, S., et al.,•"Botulinum toxin-A therapy (orpalmar and plantar hyperhidrosis," Acta Neurol Belg Dec. 2002;102(4):167-70.
Shantz, E.J., et ai, "Properties and use of Botulinum toxin and Other Microbial Neurotoxins in Medicine," Microbiol Rev. 56;80-99:1992.
Singh, "Critical Aspects of Bacterial Protein Toxins," pp. 63-84 (chapter 4) of Natural Toxins II, edited by B.R. Singh et al., Plenum Press, New York (1976).
Sloop et ai, "Reconstituted botulinum toxin type A does not lose potency in humans if it is refrozen or refrigerated for 2 weeks before use", Neurology, 48:249-53:1997.
Suputtitada A, "Local Botulinum Toxin Type A Injections in the Treatment of Spastic Toes," Am J. Phys Med Rehabil Oct. 2002; 81(10):770-775.
Weigand et ai, "'-Label/ed Botulinum A Neurotoxin: Pharmacokinetics in Cats after Intramuscular Injection," Nauny-Schmiedeberg's Arch. Pharmacol. (1976) 292:161-165.
Whalen R.L. et al., Microencapsulated Vaccines to Provide Prolonged Immunity with a Single Administration, *Asaio Journal*, J.B. Lippincott Co., Hagerstown, MD, vol. 42, No. 5, Sep. 1996, pp. M649-M654.

* cited by examiner

COSMETIC NEUROTOXIN COMPOSITIONS AND METHODS

This application is a continuation application of U.S. application Ser. No. 12/695,105, filed Jan. 27, 2010, which is a continuation of U.S. application Ser. No. 10/957,004, filed Oct. 1, 2004, now abandoned, the entire contents of which applications are incorporated herein by reference.

BACKGROUND

Skin Contour Deficiencies

For a variety of reasons, damage to the skin often results in skin contour deficiencies and other skin anomalies, including wrinkles. In order to correct contour deficiencies and other anomalies of the skin, people often resort to cosmetic surgery, such as face lifts and skin tucks and/or injection of various materials, such as collagen, silicone, and solid microparticles. U.S. Pat. No. 6,436,424 discloses injectable and swellable microspheres for dermal augmentation. Liquid compositions containing botulinum toxin have been used to treat wrinkles.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)[1] is a LD50 in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated LD50 of botulinum toxin type A of 0.3 ng equals 1 U is corrected for the fact that about 0.05 ng of BOTOX® equals 1 unit). One unit (U) of botulinum toxin is defined as the LD50 upon intraperitoneal injection into female Swiss Webster mice weighing 18 to 20 grams each.

[1] Available from Allergan, Inc., of Irvine, Calif. under the tradename BOTOX® in 100 unit vials)

Seven generally immunologically distinct botulinum neurotoxins have been characterized, these being respectively botulinum neurotoxin serotypes A, B, C1, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate LD50 for botulinum toxin type A. Moyer E et al., *Botulinum Toxin Type B: Experimental and Clinical Experience*, being chapter 6, pages 71-85 of "Therapy With Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, HC, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, HN, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype C1 was originally thought to cleave syntaxin, but was found to cleave syntaxin and SNAP-25. Each of the botulinum toxins specifically cleaves a different bond, except botulinum toxin type B (and tetanus toxin) which cleave the same bond. Each of these cleavages block the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). In 1989 a botulinum toxin type A complex has been approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type C1 has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. *Biochem J* 1; 339 (pt 1):159-65:1999, and *Mov Disord*, 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and C1 is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2); 522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165; 675-681:1897. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9); 1373-1412 at 1393; Bigalke H., et al., *Botulinum A Neurotoxin Inhibits Non-Cholinergic Synaptic Transmission in Mouse Spinal Cord Neurons in Culture*, Brain Research 360; 318-324:1985; Habermann E., *Inhibition by Tetanus and Botulinum A Toxin of the release of [3H]Noradrenaline and [3H]GABA From Rat Brain Homogenate*, Experientia 44; 224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316; 244-251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes C1, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine*, Microbiol Rev. 56; 80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1-2 \times 10^8$ LD50 U/mg or greater; purified botulinum toxin type B with an approximately 156 kD molecular weight with a specific potency of $1-2 \times 10^8$ LD50 U/mg or greater, and; purified botulinum toxin type F with an approximately 155 kD molecular weight with a specific potency of $1\text{-}2\times10^7$ LD50 U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin can also be used to prepare a pharmaceutical composition.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology,* 48:249-53:1997.

It has been reported that botulinum toxin type A has been used in clinical settings as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Supp 4): S111-S1150:1999), and in some circumstances for as long as 27 months, when used to treat glands, such as in the treatment of hyperhydrosis. See e.g. Bushara K., *Botulinum toxin and rhinorrhea*, Otolaryngol Head Neck Surg 1996; 114(3):507, and *The Laryngoscope* 109:1344-1346:1999. However, the usual duration of an intramuscular injection of Botox® is typically about 3 to 4 months.

The success of botulinum toxin type A to treat a variety of clinical conditions has led to interest in other botulinum toxin serotypes. Two commercially available botulinum type A preparations for use in humans are BOTOX® available from Allergan, Inc., of Irvine, Calif., and Dysport® available from Beaufour Ipsen, Porton Down, England. A Botulinum toxin type B preparation (MyoBloc®) is available from Elan Pharmaceuticals of San Francisco, Calif.

In addition to having pharmacologic actions at the peripheral location, botulinum toxins may also have inhibitory effects in the central nervous system. Work by Weigand et al, *Nauny-Schmiedeberg's Arch. Pharmacol.* 1976; 292, 161-165, and Habermann, *Nauny-Schmiedeberg's Arch. Pharmacol.* 1974; 281, 47-56 showed that botulinum toxin is able to ascend to the spinal area by retrograde transport. As such, a botulinum toxin injected at a peripheral location, for example intramuscularly, may be retrograde transported to the spinal cord.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

A botulinum toxin has also been proposed for or has been used to treat otitis media of the ear (U.S. Pat. No. 5,766,605), inner ear disorders (U.S. Pat. Nos. 6,265,379; 6,358,926), tension headache, (U.S. Pat. No. 6,458,365), migraine headache pain (U.S. Pat. No. 5,714,468), post-operative pain and visceral pain (U.S. Pat. No. 6,464,986), hair growth and hair retention (U.S. Pat. No. 6,299,893), psoriasis and dermatitis (U.S. Pat. No. 5,670,484), injured muscles (U.S. Pat. No. 6,423,319) various cancers (U.S. Pat. No. 6,139,845), smooth muscle disorders (U.S. Pat. No. 5,437,291), and neurogenic inflammation (U.S. Pat. No. 6,063,768). Controlled release toxin implants are known (see e.g. U.S. Pat. Nos. 6,306,423 and 6,312,708) as is transdermal botulinum toxin administration (U.S. patent application Ser. No. 10/194,805).

Additionally, a botulinum toxin may have an effect to reduce induced inflammatory pain in a rat formalin model. Aoki K., et al, *Mechanisms of the antinociceptive effect of subcutaneous Botox: Inhibition of peripheral and central nociceptive processing*, Cephalalgia 2003 September; 23(7): 649. Furthermore, it has been reported that botulinum toxin nerve blockage can cause a reduction of epidermal thickness. Li Y, et al., *Sensory and motor denervation influences epidermal thickness in rat foot glabrous skin*, Exp Neurol 1997; 147:452-462 (see page 459). Finally, it is known to administer a botulinum toxin to the foot to treat excessive foot sweating (Katsambas A., et al., *Cutaneous diseases of the foot: Unapproved treatments*, Clin Dermatol 2002 November-December; 20(6):689-699; Sevim, S., et al., *Botulinum toxin—A therapy for palmar and plantar hyperhidrosis*, Acta Neurol Belg 2002 December; 102(4):167-70), spastic toes (Supurtitada, A., *Local botulinum toxin type A injections in the treatment of spastic toes*, Am J Phys Med Rehabil 2002 October; 81(10):770-5), idiopathic toe walking (Tacks, L., et al., *Idiopathic toe walking: Treatment with botulinum toxin A injection*, Dev Med Child Neurol 2002; 44(Suppl 91):6), and foot dystonia (Rogers J., et al., *Injections of botulinum toxin A in foot dystonia*, Neurology 1993 April; 43(4 Suppl 2)).

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively).

Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153-9158: 1990.

Acetylcholine

Typically only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the bag 1 fibers of the muscle spindle fiber, by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell.

Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

U.S. Pat. No. 6,585,993 discloses a controlled release neurotoxin system. U.S. Pat. No. 6,506,399 discloses a biodegradable botulinum toxin implant. U.S. Pat. No. 6,383,509 discloses a biodegradable neurotoxin implant. U.S. Pat. No. 6,312,708 discloses a botulinum toxin implant. U.S. Pat. No. 6,306,423 discloses a neurotoxin implant Thus, there remains a need for new compositions and methods which may be used to treat skin conditions and enhance cosmetic features of individuals.

SUMMARY

The present invention addresses this need and provides new cosmetic compositions and methods that provide long lasting effective treatment of cosmetic defects.

In a broad embodiment, a composition useful for treating a cosmetic defect in an individual comprises a botulinum toxin component; and a microsphere component comprising a plurality of swellable microspheres. The botulinum toxin component can comprise one or more botulinum toxins, such as botulinum toxin type A, B, C, D, E, F, or G. The microsphere component can be understood to be a hydrogel material, and may comprise a plurality of particles of crosslinked polymers. The botulinum toxin can be mixed with, coupled to, or encapsulated by the particles.

In one embodiment, a composition useful for treating a cosmetic defect in an individual comprises a cosmetic defect treating amount of botulinum toxin type A; and a plurality of swellable microspheres effective in treating a cosmetic defect of the individual.

The present compositions provide enhanced treatment of cosmetic defects relative to substantially identical compositions without a botulinum toxin component.

The present invention also encompasses a method of treating a cosmetic defect or deficiency by administering a cosmetic composition, such as the foregoing compositions, to an individual in need of treatment, such as a person who desires such cosmetic treatment.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description and claims, particularly when considered in conjunction with the accompanying drawings.

DEFINITIONS

The following definitions apply herein.

"About" means plus or minus ten percent of the value so qualified.

"Biocompatible" means that there is no significant inflammatory or antigenic response from administration of the composition.

"Biologically active compound" means a compound which can effect a beneficial change in the subject to which it is administered. For example, "biologically active compounds" include neurotoxins.

"Effective amount" as applied to the biologically active compound means that amount of the compound which is generally sufficient to effect a desired change in the subject. For example, where the desired effect is a reduction in a wrinkle, an effective amount of the compound is that amount which causes at least a substantial reduction of the wrinkle, and without resulting in significant toxicity.

"Effective amount" as applied to a non-active ingredient constituent of an injectable composition (such as a carrier used for mixing with a botulinum toxin) refers to that amount of the non-active ingredient constituent which is sufficient to positively influence the release and/or activity of the active ingredient when administered to an individual. This "effective amount" can be determined based on the teaching in this specification and the general knowledge in the art.

"Neurotoxin" means an agent which can interrupt nerve impulse transmission across a neuromuscular or neuroglandular junction, block or reduce neuronal exocytosis of a neurotransmitter or alter the action potential at a sodium channel voltage gate of a neuron. Examples of neurotoxins include botulinum toxins, tetanus toxins, saxitoxins, and tetrodotoxin.

"Treatment" means any treatment of a disease in a mammal, and includes: (i) preventing the disease from occurring or; (ii) inhibiting the disease, i.e., arresting its development; (iii) relieving the disease, i.e., reducing the incidence of symptoms of or causing regression of the disease. Cosmetic treatment refers to reducing or treating one or more cosmetic defects or deficiencies.

"Microspheres" refers to a polymer or combinations of polymers made into bodies or elements of various sizes. The microspheres can be in any shape, although they are often in substantially spherical shape.

"Swellable" microspheres, as used herein, refers to microspheres that are capable of being enlarged in size, yet still retain substantially the same shape, upon certain conditions such as contacting physiological fluids or other aqueous fluids. Preferably, the swellable microspheres of the present invention can be enlarged to about 4 times of their original diameter or 15 times of their original volume. The degree of swelling can be controlled by controlling factors such as the solvents in which they are suspended, specific polymers used to make the microspheres and degree of crosslinking. This property enables the microspheres be easily injected through needles of 30 gauge or smaller, yet be enlarged and secured at the injection site and of sufficient size to avoid or reduce the chance of being eliminated by the immune system of the individual.

"High water absorbing polymers" as used in the present invention refers to polymers that can absorb at least 5% water by weight or that are capable of increasing the dry weight of the polymers to about 20 times of their original dry weight. The microspheres of the present compositions also comprise particles that are "hydrophilic," which, as used in the invention, means the particles can dissolve in, absorb, or mix easily with water or aqueous solution.

"Biodegradable" microspheres refer to microspheres that are capable of being absorbed by the body, chemically, physiologically, or by other biological means, over a period of time.

"Substantially spherical" generally means a shape that is close to a perfect sphere, which is defined as a volume that presents the lowest external surface area. Specifically, "substantially spherical" in the present invention means, when viewing any cross-section of the particle, the difference between the average major diameter and the average minor diameter is less than 20%. The surfaces of the microspheres of the present invention appear smooth under magnification of up to 1000 times. The microspheres of the present invention may comprise, in addition to the particles, other materials as described and defined herein.

"Dermal augmentation" in the context of the present disclosure refers to any change of the natural state of an individual's skin and related areas due to external acts. The areas that may be changed by dermal augmentation include, but not limited to, epidermis, dermis, subcutaneous layer, fat, arrector pill muscle, hair shaft, sweat pore, sebaceous gland, and subdermal musculature. Dermal augmentation is used to treat cosmetic defects and/or cosmetic deficiencies.

"Cell adhesion promoter" as used herein refers to any material that, because of its presence in or association with the microspheres, promotes or enhances the adhesiveness of cells to the surface of the microspheres. These materials are often proteins that are bound to the surface of the microspheres through covalent bonds of the proteins and the polymers.

"Therapeutic agent" as used herein refers to any substance that provides therapeutic effects to the process of dermal augmentation or biological or physiological responses to the dermal augmentation. An example of therapeutic agent is a neurotoxin which is effective in relaxing muscles. One example of a suitable neurotoxin is a neurotoxin produced by Clostridial bacteria, such as *Clostridium beratti, Clostridium butyricum, Clostridium tetani*, and *Clostridium botulinum*. As described herein, preferred compositions comprise a botulinum toxin component. A botulinum toxin component is a portion of the composition which includes one or more botulinum toxin types selected from the group consisting of botulinum toxin types A, B, C, D, E, F, and G. The botulinum toxin component may comprise a botulinum toxin produced by a Clostridial bacteria, or produced by recombinant technology. The botulinum toxin can be a recombinantly made or a hybrid botulinum toxin. In preferred compositions, the botulinum toxin component comprises a botulinum toxin type A, such as the commercially available botulinum toxin sold under the tradename, BOTOX® (Allergan, Inc., CA).

"Chemical modification" in the present invention means the changes of chemical properties and characteristics of the microspheres, either during their production process or by way of mixing or contacting them with various agents or tissues, such that the microspheres have the ability to perform, in addition to dermal augmentation, other functions once injected into the body.

DESCRIPTION

Compositions and methods have been invented which provide effective, long lasting treatment of skin or dermal conditions. The present compositions comprise swellable microspheres and one or more Clostridial neurotoxins. The present cosmetic compositions and methods may be effective in augmenting the skin of an individual, such as a person, to enhance cosmetic features of the individual. Thus, the present invention relates to cosmetic treatment of a dermal condition, such as wrinkles, other skin contour deficiencies, and the like. Or stated differently, the present invention relates to compositions and methods for treating one or more cosmetic defects of deficiencies.

In one embodiment of the present invention, a composition comprises a botulinum toxin component, and a microsphere component. The composition may be administered, such as by injection, to provide a cosmetic or therapeutic benefit to an individual. Accordingly, the composition may be useful for dermal augmentation.

The microsphere component of the composition comprises a plurality of swellable microspheres. For example, the composition comprises a plurality of microspheres that swell when in contact with an aqueous fluid, such as a physiological fluid. The composition is preferably sterile when administered to an individual. In addition, prior to administration, the composition may be provided in a lyophilized state, or may include a non-aqueous solvent component. Thus, the present compositions may be understood to comprise a botulinum toxin component, such as one or more botulinum toxins, and a hydrogel material, such as a water-swellable material. The hydrogel material may be the microspheres disclosed herein.

The botulinum toxin component may be associated with the microsphere component so that the composition is effective in enhancing or augmenting a cosmetic feature, such as a defect, of the individual. Without wishing to be bound by theory, a physiological mechanism can be proposed for the efficacy of my invention as disclosed herein for the treatment of a cosmetic defect or deficiency using a Clostridial neurotoxin. Essentially, it is hypothesized that use of a Clostridial neurotoxin, such as botulinum toxin, can inhibit release of acetylcholine from one or more nerves innervating a muscle associated with the cosmetic defect or deficiency to relax the muscle, and the microspheres of the composition can increase in size when subdermally or intradermally administered to augment the skin and reduce the cosmetic defect or deficiency, thereby treating the cosmetic defect or deficiency. Thus, the augmenting of the skin of an individual may be achieved by the combination of the swelling of the microspheres, and by the enzymatic activity of a botulinum toxin of the botulinum toxin component. As indicated herein, the botulinum toxin component of the present compositions may comprise a botulinum toxin selected from the group consisting of botulinum toxin types A, B, C, D, E, F, G, and mixtures thereof. In certain preferred compositions, the botulinum toxin component comprises only a botulinum toxin type A. Botulinum toxin type A is desirable due to its high potency in humans, ready availability, and known use for the treatment of skeletal and smooth muscle disorders when locally administered by intramuscular injection.

Although the present compositions are described with particular reference to botulinum toxins, other neurotoxins may be effective in the present compositions with or without the botulinum toxins, and such other neurotoxins are included within the scope of the present invention. Examples of other Clostridial neurotoxins within the scope of the present invention include neurotoxins made by *Clostridium butyricum* and *Clostridium beratti* species. The present invention also includes the use of (a) Clostridial neurotoxins obtained or processed by bacterial culturing, toxin extraction, concentration, preservation, freeze drying, and/or reconstitution; and/ or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

The neurotoxin may be combined with the microsphere component and stored for prolonged periods of time prior to administration to an individual, or may be combined with the microsphere component in an injectable composition, for example, immediately prior to administration to an individual. Care should be taken to reducing the amount of liquid, such as an aqueous liquid, in the compositions comprising a microsphere component since the microsphere component has a plurality of swellable microspheres.

The amount of the Clostridial toxin in the compositions or administered according to the present methods can vary according to the particular characteristics of the skin disorder being treated, including its severity and other various patient variables including size, weight, age, and responsiveness to therapy. To guide the practitioner, typically, no less than about 1 unit and no more than about 50 units of a botulinum toxin type A (such as BOTOX®) is administered per injection site (i.e. to each skin location injected), per patient treatment session. For a botulinum toxin type A such as DYSPORT®, no less than about 2 units and no more about 200 units of the botulinum toxin type A are administered per administration or injection site, per patient treatment session. For a botulinum toxin type B such as MYOBLOC®, no less than about 40 units and no more about 2500 units of the botulinum toxin type B are administered per injection site, per patient treatment session. Less than about 1, 2 or 40 units (of BOTOX®, DYSPORT® and MYOBLOC® respectively) can fail to achieve a desired therapeutic effect, while more than about 50, 200 or 2500 units (of BOTOX®, DYSPORT® and MYOBLOC® respectively) can result in clinically observable and undesired muscle hypotonicity, weakness and/or paralysis.

More preferably: for BOTOX® no less than about 2 units and no more about 20 units of a botulinum toxin type A; for DYSPORT® no less than about 4 units and no more than about 100 units, and; for MYOBLOC®, no less than about 80 units and no more than about 1000 units are, respectively, administered per injection site, per patient treatment session.

Most preferably: for BOTOX® no less than about 5 units and no more about 15 units of a botulinum toxin type A; for DYSPORT® no less than about 20 units and no more about 75 units, and; for MYOBLOC®, no less than about 200 units and no more than about 750 units are, respectively, administered per injection site, per patient treatment session.

It is important to note that there can be multiple injection sites (i.e. a pattern of injections) for each patient treatment session.

Thus, the botulinum toxin component of the present compositions may comprise an amount of botulinum toxin in a range from about 1 unit to about 50,000 units. The amount of botulinum toxin component present in the composition will vary depending on the type of botulinum toxin provided, such as the serotype or strain of botulinum toxin, and the amount of the composition to be administered to a patient. In certain compositions, the botulinum toxin comprises an amount of 10 units to about 2,000 units of a botulinum toxin type A. In other compositions, the botulinum toxin component comprises an amount of botulinum toxin in a range from about 100 units to about 30,000 units of a botulinum toxin type B. Preferably, the present compositions only comprise biologically active botulinum toxins as a therapeutic agent. For example, the present compositions are substantially free of a botulinum toxoid.

The present cosmetic compositions also comprise swellable microspheres. The microspheres of the present compositions are also preferably hydrophilic, non-toxic, and, substantially spherical. The microspheres are at least a portion, including an entire portion, of a microsphere component. The microsphere component thus has an average microsphere diameter (e.g., the average diameter of a population of microspheres present in the composition). In certain embodiments of the present compositions, the average microsphere diameter after administration of the composition to an individual is between about one to about four times greater than the average microsphere diameter before administration. The increase in average microsphere diameter is due to the swellability of the microspheres. For example, as the composition is administered to an individual, the microspheres contact a fluid, such as an aqueous body fluid. The microspheres incorporate the fluid and swell as a result.

The microspheres of the present compositions may comprise a plurality of crosslinked polymers. Such polymers may be crosslinked using conventional methods routinely known to persons of ordinary skill in the art. The polymers of the microspheres may be hydrophilic. Thus, as described herein, the microsphere component of the present compositions may be a hydrogel material. The microspheres swell when the contact an aqueous fluid. As understood by a person skilled in the art, the degree of swelling of crosslinked polymers generally depends on the properties of the polymeric materials such as their ionic character, the hydrophilicity of the polymeric materials, and the degree of crosslinking. Properties, such as salt and ionic concentration and level of pH, of the solvent in which the microspheres are suspended or with which the microspheres are contacting also affect the degree of swelling.

By controlling the size and the degree of swelling of certain crosslinked and swellable polymers, safe, effective, and long lasting dermal augmentation can be achieved using these microspheres. Generally, polymeric materials having high water absorbing ability are first chosen. The swellability of these polymers can be further manipulated by controlling the polymer's ionic character and the degree of crosslinking by methods known to a skilled person.

The microspheres of the present invention can be either anionic or cationic. Cationic microspheres may be desirable due to their superior ability of promoting cell adhesion. The crosslinking degree of the microspheres can be changed either chemically or through radiation. A variety of crosslinking agents may be used, including, but not limited to, tetraethylene glycol diacrylate, tetraethylene glycol dimethacrylate, ethylene glycol dimethacrylate, methacrylate, and pentaerythritol dimethacrylate. The microspheres of the invention may comprise from about 0.5% to about 20%, by molecular weight, of crosslinkers. For example, the microspheres may comprise from about 1% to about 5%, by molecular weight, of crosslinkers.

The swelling of the microspheres comprising these polymers can be further controlled by controlling the solvent in which the microspheres are suspended. This can be achieved through two steps as disclosed herein. First, the size of the microspheres before injection are controlled by using appropriate solvents, salt concentration and pH level according to the specific microspheres used. The microspheres before injection may either remain in their original size or swell to certain degree due to their contact with the solvent. The pre-injection swelling is controlled so that the microspheres are easily injectable through 30 gauge or smaller needles. Second, after injection and upon contacting with tissues at injection site, the microspheres may further swell into predetermined size or retain their pre-injection size, either of which size will allow the microspheres to be secured at the site of injection and achieve desired dermal augmentation effect. The degree of pre-injection swelling, and thus the post-injection swelling, is determined by the particular microspheres used and the nature and location of the skin deficiencies being treated.

Microspheres for use in the present compositions may have diameters range from about 10 µm to about 400 µm before swelling. For example, before swelling, the diameters of the microspheres may range from about 10 µm to about 200 µm, such as, from about 10 µm to about 120 µm. After injection and swelling, the microspheres generally have average diameters larger than 40 µm, for example larger than about 50 µm, such as larger than about 70 µm. The microspheres of the present compositions are capable of swelling to about four times their original diameters or about fifteen times their original volume. The full swollen size of the microspheres after administration may be controlled, by various means discussed herein, so that the microspheres are secured at the site of injection while minimizing or reducing potential injuries to the tissues. Further, the full swollen sizes of the microspheres after injection are predetermined based on factors such as the physiological conditions of the injection site, the original microspheres sizes, the solvent used and the pre-injection swelling of the microspheres. Thus, a specific injection plan can be designed according to the particular dermal augmentation need of the case. These sizes and properties of the microspheres are advantageous in that they enable the microspheres to be easily injectable through needles of 30 gauge or smaller, yet the microspheres are large enough so that they will be secured at the site of injection and will not be digested or eliminated by macrophage or other elements of the immune system.

The microspheres also appear to be resistant to injection force created by 30 gauge or smaller needles and to the muscle contraction stress generated during and after the injection process. The microspheres are also thermally stable which allows for easy, convenient sterilization, and frozen storage for the preparation of injection.

Many types of crosslinked polymers having high water absorbing ability are suitable for use in the present compositions. Such crosslinked polymers are preferably non-toxic to tissues and cells and are biocompatible. Preferably, the polymers are selected from the group consisting of sodium acrylate polymer, acrylamide polymers, acrylamide derivative polymers or copolymers, sodium acrylate and vinyl alcohol copolymer, saponification products of copolymer of vinyl acetate and acrylic acid ester, vinyl acetate and acrylic acid ester copolymer, vinyl acetate and methyl maleate copolymer, isobutylene-maleic anhydride crosslinked copolymer, starch-acrylonitrile graft copolymer and its saponification products, crosslinked sodium polyacrylate polymer, and crosslinked polyethylene oxide.

The microspheres of the present invention can be biodegradable or nonbiodegradable. Further, the microspheres of the present invention are thermally stable which allows for easy, convenient sterilization, and frozen storage. The microspheres for use in the present invention are also stable in suspension which allows the microparticles to be formulated and stored in suspension and injected with different liquids or oils. More specifically, the hydrophilic nature of the microspheres permits placing them in suspension, and in particular, in sterile form of injectable solutions, while avoiding the formation of aggregates or adhesion to the walls of storage containers and implantation devices, such as catheters, syringes, needles, and the like.

The microspheres of the present invention may contain within their structure or on their surfaces other chemicals or agents, therefore displaying particular properties, such as therapeutic, radio-pacifying, and contrasting effects; targeting promotion of cell adhesion; and capability of being chemically modified. Thus, the microspheres may comprise an agent selected from the group consisting of radio-pacifying agents, contrast agents, targeting agents, and mixtures thereof. In one embodiment of the present compositions, the microspheres comprise a cell adhesion promoter. In another embodiment, the microspheres may comprise cells provided on the surface or surfaces of the microspheres. The cells may be autologous cells.

The microspheres of the present invention may further associated with contrast medium or agent. Contrast media useful within the present invention can be found in Dawson et al. Contrast Medium in Practice (Springer-Verlag, 1994). Contrast media include, and are not limited to, ultrasonic media, superparamagnetic media, and gadolinium contrast media. Preferably, the contrast media include any media that contain barium or iodine salts, such as high molecular weight salts, including acylamino-e-propion-amido-3-triiodo-2,4,6-benzoic acid, which can be prepared under the conditions described by Boschetti et al. (Bull. Soc. Chim., No. 4 France, (1986)). In the case of barium or magnetite salts, they can be directly introduced in powdered form in the initial monomer solution.

In another embodiment of the invention, the microspheres have specific properties suitable for cell adhesion and cells growth promotion, making the microspheres particularly useful for certain dermal augmentation. Cells can be associated with the microspheres, through adhesion or other means, prior to injection. The cells may be autologous cells obtained from or derived from the individual receiving the cosmetic composition. These autologous cells are preferably the same type of cells that need to be repaired in the dermal augmentation, such as fat cells, muscle cells, subcutaneous cells, dermal cells, epidermal cells, or mixtures thereof. The autologous cells may also preferably be cells that enhance or promote the growth or connection of cells or tissues, such as fibroblast cells.

Various types of cell adhesion promoters or agents well known in the art may be used in the microspheres of the present compositions. For example, cell adhesion agents can be selected from collagen, gelatin, glucosaminoglycans, fibronectins, lectins, polycations (such polylysine, chitosan and the like), extracellular matrix, degradation products of cells or tissues, or any other natural or synthetic biological cell adhesion agent.

Cell adhesion promoters or marking agents can be introduced on microspheres by chemical coupling procedures well known in affinity chromatography, referred to by the term "ligand immobilization". Another method of introduction is by diffusion within the gel network that constitutes the bead and then trapping the diffused molecules in place by precipitation or chemical cross-linking.

The neurotoxin, such as the botulinum toxin, of the present compositions is associated with the microsphere component to provide effective treatment of a dermal condition. The neurotoxin can be mixed with the microspheres so that the neurotoxin and microspheres are physically distinct, but cooperatively interact to provide the desired cosmetic benefits disclosed herein. Or, the neurotoxin may be coupled with the microspheres. For example, the microspheres can be chemically modified so that they will be physically coupled to the neurotoxin. For example, the neurotoxin may be covalently coupled to the microspheres. Alternatively, the neurotoxin can be incorporated into a polymeric network of the microspheres so that the neurotoxin is not releasable from the microspheres until the microspheres swell. Or, the neurotoxin may be complexed with the microspheres as a result of ionic interactions that are not covalent bonds.

Incorporation of the neurotoxins into the microspheres of the present compositions can be accomplished using any routine method known to persons of ordinary skill in the art. For example, the incorporation can be accomplished by mixing dry microspheres with solutions of the neurotoxin in an aqueous or hydro-organic solution. The microspheres swell by adsorbing the solutions and incorporate the neurotoxin into the microparticle network. The neurotoxin may remain inside the microsphere due to an active mechanism of adsorption essentially based on ion exchange effect.

Microspheres of the present invention may further possess the property of non-aggregating, which usually results from an ionic charge of the microspheres. This property facilitates injection and more effective dermal augmentation, especially in situations where cells are associated with the microspheres. This property is important to dermal augmentation of the present invention because it makes injection of the microspheres through 30 gauge or smaller needles possible and easier. This property of the microspheres also prevents them from aggregating or adhering to syringe or needle walls or other device used in the process.

The microspheres of the present compositions can be obtained by standard methods of polymerization described in the art such as French Patent 2,378,808 and U.S. Pat. Nos. 5,648,100 and 5,635,215. In general, the polymerization of monomers in solution is carried out at a temperature ranging between about 0° C. and about 100° C., for example between about 40° C. and about 60° C., in the presence of a polymerization reaction initiator.

Microspheres can also be prepared by suspension polymerization, drop-by-drop polymerization or any other method known to a person of ordinary skill in the art. The mode of microsphere preparation selected will usually depend upon the desired characteristics, such as microsphere diameter and chemical composition, for the resulting microspheres. The microspheres can also be made by methods of polymerization described in the art (see, e.g., E. Boschetti, Microspheres for Biochromatography and Biomedical Applications. Part I, Preparation of Microbeads In: Microspheres, Microencapsulation and Liposomes, John Wiley & Sons, Arshady R., Ed., 2:171-189 (1999)). Microspheres can also be prepared starting from an aqueous solution of monomers containing adhesion agents such as collagen (gelatin is a denatured collagen). The solution is then mixed with a non-aqueous-compatible solvent to create a suspension of droplets, which are then turned into solid gel by polymerization of monomers by means of appropriate catalysts. Microspheres are then collected by filtration or centrifugation and washed.

The present compositions may comprise a carrier component. The carrier component of certain useful compositions may be an aqueous composition, and in certain embodiments, the carrier component is saline. However, many types of emulsions and solvents can be used as a biocompatible carrier for the present compositions. The solvent may be in such a condition that the microspheres can be uniformly suspended and, more importantly, that the swelling of the microspheres can also be controlled by adjusting the solvent, the salt and ionic concentration, the pH value, or combinations thereof. Some additional suitable solvents for the present compositions include aqueous based solutions such as PBS solutions, alcohol based solutions, and other biocompatible hydro-organic solutions known in the art.

Salt concentration and pH level of the solvent are useful to control the degree of swelling of the microspheres once they are suspended in the solvent. The presence of cations such as sodium, potassium, calcium, magnesium, iron, zinc, and ammonium has various level of effects on the degree of swelling of the microspheres depending on the specific polymer and salt used. The degree of swelling of the microspheres is partially controllable by changing the balance of smaller cations and larger cations between the solvent and the microspheres. A salt level of 0.01 M to 5 M is effective to keep the microspheres from swelling. While the microspheres swell uninhibitedly under a neutral pH level, the change of pH level may affect the degree of swelling. For the anionic microspheres, the preferred pH level to shrink the microspheres or to keep them from swelling is from about 0.5 to 5. For the cationic microspheres, a pH level ranges from about 6 to about 11 will shrink the microspheres or keep them from swelling. Thus, acidic pH's may provide beneficial effects when the composition comprises both anionic microspheres and botulinum neurotoxin.

Upon suspension in the solvent and before injection, the microspheres may swell and the degree of swelling is controlled by the solvent and other conditions, such as time and temperature of suspension. The pre-injection swelling of the microspheres is further determined by the desired after-injection-swelling for the microspheres. Thus, microspheres that have obtained high degree of swelling before injection will swell little after injection, whereas microspheres that have swelled little before injection will obtain a higher degree of swelling after injection. The size of the microspheres before, during and after injection is generally controlled such that they are easily injectable through 30 gauge or smaller needles yet become secured at the site of injection.

The biocompatible carrier of the present invention can also be an emulsion. In this embodiment, the properties of the microspheres, especially their size and degree of swelling, are preserved through the well controlled balance between the aqueous and the non-aqueous phases in the emulsion.

The present compositions may comprise a botulinum toxin component associated with a microsphere component so that the composition is effective in augmenting a cosmetic feature of an individual for a period of time ranging from about one month to about six years after administration to the individual. Advantageously, the present compositions provide enhanced cosmetic effects relative to substantially identical compositions without a neurotoxin, such as a botulinum toxin. For example, the present compositions may provide a cosmetic enhancement or augmentation due to the paralytic effects of the neurotoxin, and the swellable nature of the microspheres. In addition, the botulinum toxin component may be associated with the microsphere component so that the botulinum toxin retains a enzymatic activity after passing through a needle of about 30 gauge or smaller.

Thus, the present injectable composition comprise microspheres in an amount from about 10% to about 90% by weight and the biocompatible carrier in an amount from about 10% to about 90% by weight. For example, the amount ranges from 10% to 50% by weight for microspheres and from 50% to 90% for biocompatible carrier. The relative amount of the microspheres and the carrier changes according to the need of the specific dermal augmentation performed, depending on factors such as size of needle used, type of microspheres and carriers used, type of skin deficiency, area of injection, type of tissue or cells being augmented, and whether cells are associated with the microspheres prior to injection.

To prepare a suspension of the microspheres, dried sterilized microspheres can be mixed with a desired solvent at a pre-determined time such that the pre-injection swelling of the microspheres is controlled. The solvent can be pre-sterilized or the suspension of microspheres and the solvent can be sterilized together before injection thereof. Factors such as the material, size and crosslinking degree of the microspheres; the type, volume, salt concentration, pH level and temperature of the solvent; and the time of mixing are all considered before an injectable suspension is made and the injection is carried out thereafter.

The composition of the present invention is easily injectable, through needles of 30 gauge or smaller, into all parts of an individual, such as a human patient, who desires treatment of a cosmetic defect or deficiency. The composition can be administered, such as by injection, without causing significant pain or discomfort. This is due to, among other factors, the size and the physical resiliency of the microspheres, the biocompatible nature of the carrier, and the amount of the composition administered in accordance with the character and location of the skin deficiency.

In another embodiment of the present invention, a composition useful for dermal augmentation in an individual comprises a dermal augmenting amount of a botulinum toxin type A, and a plurality of swellable microspheres effective in augmenting a dermal condition of the individual. Such a composition may be an injectable composition effective in treating wrinkles. For example, such a composition may be effective in providing long-lasting treatment of marrionette lines, glabellar lines, crows feet, brow furrows, or combinations thereof. The botulinum toxin type A is typically provided in an amount effective in providing a longer lasting anti-wrinkle effect relative to a substantially identical composition without a botulinum toxin. In certain compositions, the composition also comprises at least one additional botulinum toxin, such as a botulinum toxin type B, C, D, E, F, or G. As discussed herein, the plurality of microspheres of the composition has an average microsphere diameter, and in certain compositions, the average microsphere diameter increases after injection into the individual from about one time to about four times the average microsphere diameter prior to injection.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14th edition, published by McGraw Hill). For example, the route and dosage for administration of a Clostridial neurotoxin according to the present disclosed invention can be selected based upon criteria such as the solubility characteristics of the neurotoxin chosen as well as the intensity and scope of the cosmetic condition being treated.

In another embodiment of the present invention, a method for treating a dermal condition, such as a wrinkle or other skin deficiency, comprises administering the composition disclosed herein to an individual in need of treatment, or who desires such treatment for the dermal condition. As discussed herein, the present compositions are effective in treating dermal conditions including marrionette lines, glabellar lines, crows feet, brow furrows, and the like, and combinations thereof. The compositions can be injected into the individual using a needle or a needleless device. In certain embodiments, the method comprises subdermally injecting the composition in the individual. For example, the administering may comprise injecting the composition through a needle no greater than about 30 gauge. In certain embodiments, the method comprises administering a composition comprising a botulinum toxin type A. The present methods may be effective in treating a dermal condition for a longer time relative to administering a substantially identical composition without a botulinum toxin.

In a further embodiment, the method may include an additional step of administering a botulinum toxin to the individual. Thus, the individual may receive be administered a composition comprising a botulinum toxin and a plurality of swellable microspheres, and a different composition only comprising a botulinum toxin as a therapeutic or cosmetic agent.

Injection of the compositions can be carried out by syringe, catheters, needles and other means for injecting or infusing microspheres in a liquid medium. The injection can be performed on any area of the mammal's body that is in need of treatment, including, but not limited to, face, neck, torso, arms, hands, legs, and feet. The injection can be into any position in the specific area such as epidermis, dermis, fat, or subcutaneous layer. A particular effective position of injection according the present invention's methods, is the subcutaneous layer, which allows the microspheres and the associated agents and cells perform more effectively.

The frequency and the amount of injection under the present invention is determined based on the nature and location of the particular skin deficiency being treated. Generally, because of the stable and long lasting character of the present invention's injectable composition, multiple injections are not necessary. In certain cases, however, repeated injection may be desired to achieve optimal results. The frequency and the amount of the injection for each particular case is determined by the person of ordinary skill in the art.

As disclosed herein, after injection, the microspheres become secured at the position of the injection. The microspheres are not significantly digested or eliminated by macrophage or other elements of the immune system. Furthermore, the microspheres will not displace or slide away from the position of injection. The secure positioning of the microspheres near the injection site is due to, among other factors, their size, physical resiliency, and hydrophilicity. The swellability of the microspheres at the site of injection is important in helping secure the microspheres at the site of injection. Upon contacting the physiological fluids and the cells at the site of injection, the microspheres may further swell if there is no pre-injection swelling or the swelling is controlled to a lower level. The physiological condition, including salt concentration (e.g., sodium and potassium) and pH level, may further help the microspheres swell to the desired size.

This property of the microspheres allows precise control of the injection and makes it possible that the microspheres work together at position of injection and provide a scaffold for effective dermal augmentation. Because of the precision of the injection and the securing of the microspheres at the site of injection provided by the invention, it is now possible to create a scaffold of microspheres at the site of injection without forming a scaffold of the microspheres before injection. The "injectable scaffold" comprising a Clostridial neurotoxin component is especially advantageous over prior art in which surgical procedures are necessary in order to implant a scaffold for certain dermal augmentation, or require separate administration of a botulinum toxin composition. This discovery significantly reduces the complexity of dermal augmentation when a scaffold is desired for more effective dermal augmentation in certain cases. This unique contribution of the present invention to dermal augmentation and the treatment of skin deficiencies is made possible, in part, by the well controlled size and degree of swelling of the microspheres, as well as the neurotoxic effects of the neurotoxin, as discussed above. The ability of forming a scaffold at the injection site without forming a scaffold before the injection makes the microspheres and neurotoxin of the present invention particularly effective in providing dermal augmentation. The size of the scaffold is determined by the amount and frequency of the injection, which is in turn determined by the nature and location of the skin deficiency being treated.

The present methods are particularly suitable for treatment of skin contour deficiencies, which are usually results of aging, environmental exposure, weight loss, child bearing, injury, surgery, or combinations thereof. Aging and environmental exposure often cause wrinkles on various positions of the skin. Weight loss and child bearing, on the other hand, often cause stretch marks on various positions of the skin, especially on stomach, areas of the lower body, and legs. Injury and surgery often result in scars in areas of injury and operation. Specific contour deficiencies suitable for treatment by the present invention's method include, but not limited to, frown lines, worry lines, wrinkles, crow's feet, marionette lines, stretch marks, and internal and external scars including scars resulted from injury, wounds, accidents, bites, surgery. The present methods advantageously provide dermal augmentation treatment for these various contour deficiencies in an effective, longer lasting, and stable manner than previous compositions. Particularly suitable for treatment according to the present invention are contour deficiencies of such areas as eyes, cheeks, nose, lips, forehead, and neck.

The present invention also provides method for treating skin deficiencies, especially deficiencies caused by diseases such as acne and cancer. These deficiencies can be direct or indirect results of the diseases, such as deficiencies caused by the treatment of the diseases.

The present invention further provides method of causing dermal augmentation by injecting the injectable composition not directly into the body, but extracorporeally into organs, components of organs, or tissues prior to the inclusion of said tissues, organs or components of organs into the body.

A kit for performing dermal augmentation is also encompassed by the present disclosure. The kit comprises a 30 gauge or smaller needle and a corresponding syringe, wherein the syringe optionally contains a composition comprising biocompatible, swellable, hydrophilic, non-toxic and substantially spherical microspheres and a biocompatible carrier. The kit also comprises a Clostridial neurotoxin composition, such as a botulinum toxin composition. The neurotoxin composition may be provided in the syringe with the microspheres, but preferably, the neurotoxin composition is mixed with the microsphere composition immediately prior to administration to the individual. The composition is injectable through the needle and the microspheres are not capable of being digested or eliminated by macrophage or other elements of said mammal's immune system. Alternatively, the dermal augmentation kit comprises a 30 gauge or smaller needle, a corresponding syringe, and separate containers containing the microspheres in dried form and the biocompatible solvent. The dried sterilized microspheres and the solvent are ready to be mixed for injection either in their respective containers or in the syringe. These dermal augmentation kits are sterile and ready to use. The kits are designed in various forms based the sizes of the syringe and the needles and the volume of the injectable composition contained therein, which in turn are based on the specific skin deficiencies the kits are designed to treat.

EXAMPLES

The following non-limiting examples provide those of ordinary skill in the art with specific preferred methods to treat conditions within the scope of the present invention and are not intended to limit the scope of the invention. In the following examples various modes of non-systemic administration of a Clostridial neurotoxin can be carried out.

Example 1

Botulinum Toxin Cosmetic Compositions

In a beaker containing 100 ml of demineralized water, 58 g of sodium chloride and 27 g of sodium acetate are dissolved. 400 ml of glycerol is added and then the pH is adjusted between 5.9 and 6.1. Then 90 g of N-tris-hydroxy-methyl methylacrylamide, 35 mg of diethylaminoethylacryl-amide and 10 g of N,N-methylene-bis-acrylamide are added. The composition is heated at 60-70° C. and 100 mo of a hot 300 mg/ml gelatin solution is added. The total volume of the mixture is adjusted to 980 ml by addition of hot water and then 20 ml of a 70 mg/ml ammonium persulfate solution and 4 ml of N,N,N',N'-tetramethylethylenediamine are added.

This solution is poured into paraffin oil at 50-70° C. stirring. After a few minutes, the polymerization reaction of acrylic monomers is manifested by an increase of temperature. The microspheres are then recovered by decanting, washed carefully, screened and sterilized in an autoclave in a buffered medium.

Those microspheres, after screen calibration, possess the characteristics desired for dermal augmentation.

The microspheres are combined with botulinum toxin type A (e.g., BOTOX®) in a lyophilized form, and are stored dry at −4° C. for several months. The microspheres and botulinum toxin type A are solubilized with saline before administration to an individual.

Example 2

The procedure of Example 1 is followed, using botulinum toxin type B instead of botulinum toxin type A.

Example 3 to 7

The procedure of Example 1 is following using one of botulinum toxin types C, D, E, F, and G instead of botulinum toxin type A.

Example 8

The procedure of Example 1 is followed with the addition of a second botulinum toxin other than type A.

Example 9

Use of Botulinum Toxin Type A and Swellable Microspheres to Treat Marrionette Lines A 48 year old woman with marrionnette lines seeks treatment from her physician. The woman inquires about BOTOX® injections. The physician recommends administration of a new product which utilizes both botulinum toxin and swellable microspheres. The woman agrees. The composition of Example 1 is injected into the depressor anguli oris muscle on each side of the woman's mouth. Each injection site receives about 10 units of botulinum toxin. Within about 7 days, the marrionnette lines begin to disappear. The marionnette lines remain reduced for about 2 years after that single treatment.

Example 10

Use of Botulinum Toxin Type A and Swellable Microspheres to Treat Glabellar Lines A 32 year old man with brow furrows seeks BOTOX® treatment from his physician. The physician recommends a new product which utilizes both botulinum toxin and swellable microspheres. The composition of Example 1 is injected into the corrugator and procerus muscles of the man's forehead. Each injection site receives about 5-10 units of botulinum toxin. Within about 3 days, the glabellar lines begin to disappear. The glabellar lines completely disappear in about 14 days and remain reduced for about 1 year after that single treatment.

Example 11

Use of Botulinum Toxin Type A and Swellable Microspheres to Treat Crows Feet

A 57 year old man with crows feet resulting from years of sun exposure seeks treatment from his physician. The physician recommends a product which utilizes both botulinum toxin and swellable microspheres. The composition of Example 1 is injected subdermally on either side of the patient's eyes. Each injection site receives about 3 units of botulinum toxin, with several injections made on either side of the eye. The crows feet disappear within about 10 days after treatment, and remain reduced for six months.

Example 12

Use of Botulinum Toxin Type A and Swellable Microspheres for Brow Lift

A 60 year old woman presents with eyebrows extending below her brow bone. Her physician recommends a product which utilizes both botulinum toxin and swellable microspheres. The composition of Example 1 is injected subdermally above each eye. Each injection site receives about 10 units of botulinum toxin, with several injections made on either side of the eye. The drooping of the brow is reduced within about 14 days, and is substantially alleviated for 1 year after administration.

In each of the examples 9-12 above a botulinum toxin type B, C, D, E, F or G can be substituted for the botulinum toxin type A used above, for example by use of 250 units of a botulinum toxin type B. The specific amount of a botulinum toxin (such as BOTOX® administered depends upon a variety of factors to be weighed and considered within the discretion of the attending physician and in each of the examples insignificant amounts of botulinum toxin enter appear systemically with no significant side effects.

The present compositions and methods may provide one or more of the following advantages:

1. the injected compositions are not easily displaced within the tissues in which they were originally injected,
2. the injected compositions are not readily eliminated either biochemically or through macrophage or other elements of the immune system,
3. the compositions include materials of sufficient size to be injected through 30 gauge or smaller needles,
4. the microspheres are flexible and not fragile, facilitating easy injection without being broken,
5. the injected microspheres are not irregularly shaped and do not clump together,
6. the injected compositions provide enhanced duration of therapy or cosmetic improvements relative to materials without a neurotoxin, and
7. the injected compositions provide enhancements in the therapeutic or cosmetic outcome due to the synergistic effects provided by the swellable microspheres and the neurotoxins, thus, the cosmetic defects can be dramatically reduced or eliminated.
8. the cosmetic defect can be reduced or eliminated for at least about two weeks to about six years upon use of the present compositions.
9. few or no significant undesirable side effects occur from intramuscular (or intradermal or subdermal) injection or implantation of the Clostridial neurotoxin.
10. the present methods can result in the desirable side effects of a more positive attitude, and an improved quality of life.

These benefits, whether alone or in combinations, enhance the effectiveness of the treatment and are safe, more convenient and comfortable for patients.

Although the present invention has been described in detail with regard to certain preferred compositions and methods, other embodiments, versions, and modifications within the scope of the present invention are possible. For example, a wide variety of neurotoxins can be effectively used in the methods of the present invention. Additionally, the present invention includes local administration methods to alleviate a cosmetic defect or deficiency wherein two or more neurotoxins, such as two or more botulinum toxins, are administered concurrently or consecutively. For example, botulinum toxin type A can be administered until a loss of clinical response or neutralizing antibodies develop, followed by administration of botulinum toxin type B. Alternately, a combination of any two or more of the botulinum serotypes A-G can be locally administered to control the onset and duration of the desired cosmetic result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect.

My invention also includes within its scope the use of a neurotoxin, such as a botulinum toxin, and swellable microspheres in the preparation of a medicament for the treatment of a cosmetic defect or deficiency, by local administration of the composition.

All references, articles, patents, applications and publications set forth above are incorporated herein by reference in their entireties.

Accordingly, the spirit and scope of the following claims should not be limited to the descriptions of the preferred embodiments set forth above.

What is claimed is:

1. A composition useful for treating a cosmetic defect in an individual, comprising a botulinum toxin component; and a microsphere component comprising a plurality of swellable microspheres; the composition being free of a botulinum toxoid.

2. The composition of claim 1, wherein the botulinum toxin component comprises a botulinum toxin selected from the group consisting of botulinum toxins types A, B, C, D, E, F, G, and mixtures thereof.

3. The composition of claim 1, wherein the botulinum toxin component comprises only botulinum toxin type A.

4. The composition of claim 1, wherein the botulinum toxin component comprises an amount of botulinum toxin in a range from about 10 units to about 2,000 units of a botulinum toxin type A.

5. The composition of claim 1, wherein the botulinum toxin component comprises an amount of botulinum toxin in a range from about 100 units to about 30,000 units of a botulinum toxin type B.

6. The composition of claim 1, wherein the microsphere component has an average microsphere diameter, and the average microsphere diameter after administration to the individual is between about one to about four times greater than the average microsphere diameter before administration.

7. The composition of claim 1, wherein the microspheres comprise an agent selected from the group consisting of radio-pacifying agents, contrast agents, targeting agents, and mixtures thereof.

8. The composition of claim 1, further comprising a carrier component.

9. The composition of claim 8, wherein the carrier component is an aqueous composition.

10. The composition of claim 8, wherein the carrier component is saline.

11. The composition of claim 1, wherein the composition is an injectable composition effective in treating wrinkles.

12. The composition of claim 11, wherein the wrinkles are selected from a group consisting of marrionette lines, glabellar lines, crows feet, brow furrows, and combinations thereof.

13. The composition of claim 11, wherein the plurality of microspheres have an average microsphere diameter, and wherein the average microsphere diameter increases after injection into the individual from about one time to about four times the average microsphere diameter prior to injection.

14. The composition of claim 1, further comprising at least one additional botulinum toxin selected from the group consisting of botulinum toxin types B, C, D, E, F, and G.

15. A method of treating a cosmetic defect, comprising administering the composition of claim 1 to an individual.

16. The method of claim 15, wherein the cosmetic defect is a wrinkle.

17. The method of claim 15, wherein the cosmetic defect is a condition selected from the group consisting of marionette lines, glabellar lines, crows feet, brow furrows, and combinations thereof.

18. The method of claim 15, wherein the administering comprises injecting a composition comprising a botulinum toxin type A.

* * * * *